United States Patent [19]
Portney

[11] Patent Number: 5,088,809
[45] Date of Patent: Feb. 18, 1992

[54] TELEDIOPTRIC LENS SYSTEM

[75] Inventor: Valdemar Portney, Irvine, Calif.

[73] Assignee: Allergan, Inc., Irvine, Calif.

[21] Appl. No.: 690,814

[22] Filed: Apr. 23, 1991

Related U.S. Application Data

[62] Division of Ser. No. 141,482, Jan. 5, 1988, Pat. No. 5,030,231.

[51] Int. Cl.$^5$ .............................................. G02C 1/00
[52] U.S. Cl. ....................................... 351/158; 351/41
[58] Field of Search ...................... 623/6; 351/41, 158, 351/167; 350/204, 145

[56] References Cited

U.S. PATENT DOCUMENTS

| | | | |
|---|---|---|---|
| 2,024,322 | 12/1935 | Wittig | 351/158 X |
| 2,389,428 | 11/1945 | Glasser | 351/158 |
| 3,169,247 | 2/1965 | Davis et al. | 351/167 |
| 3,273,456 | 9/1966 | Feinbloom | 351/158 X |
| 4,073,578 | 2/1978 | Welsh | 351/167 |
| 4,074,368 | 2/1978 | Levy, Jr. et al. | 623/6 |
| 4,155,626 | 5/1979 | Grech | 351/41 X |
| 4,181,409 | 1/1980 | Whitney et al. | 351/167 |
| 4,637,696 | 1/1987 | Wilkins | 351/41 |
| 4,666,446 | 5/1987 | Koziol et al. | 623/6 |
| 4,710,197 | 12/1987 | Donn et al. | 623/6 |
| 4,720,286 | 1/1988 | Bailey et al. | 623/6 |
| 4,863,468 | 9/1989 | Feinbloom et al. | 623/6 |

FOREIGN PATENT DOCUMENTS

| | | |
|---|---|---|
| 63321 | 6/1986 | Japan . |
| WO8301566 | 5/1983 | PCT Int'l Appl. . |
| WO8704264 | 7/1987 | PCT Int'l Appl. . |
| 400610 | 4/1966 | Switzerland . |
| 930219 | 7/1963 | United Kingdom . |

OTHER PUBLICATIONS

"Use of Low-Magnification Telescopes as Optometers in Low Vision", George Woo, O.D., Ph.D., *Optometric Monthly*, May 1978, pp. 147-151.

*Primary Examiner*—Ronald Frinks
*Attorney, Agent, or Firm*—Gordon L. Peterson

[57] ABSTRACT

An ocular telescopic lens system for low-vision conditions such as macular degeneration includes an intraocular lens having a converging lens portion and a diverging lens portion, and multiple-element spectacles having anterior and posterior lenses arranged to converge light toward the diverging lens portion. The intraocular lens includes an optic with a generally continuous rearward surface that combines with a first portion of the forward surface as the converging lens portion and with a second portion of the forward surface as the diverging lens portion, while the anterior and posterior lenses of the spectacles may have concave surfaces, combine to serve as an objective lens, and provide at least +8 diopter power. Mounting components are included for mounting the anterior and posterior lenses on a spectacle frame so that light passes first through the anterior lens and then through the posterior lens in traveling to the eye of a user, and these components may be configured to enable adjustment of the distance by which the anterior lens and the posterior lens are separated while maintaining the anterior lens fixed relative to the spectacle frame so as not to vary the vertex distance.

5 Claims, 4 Drawing Sheets

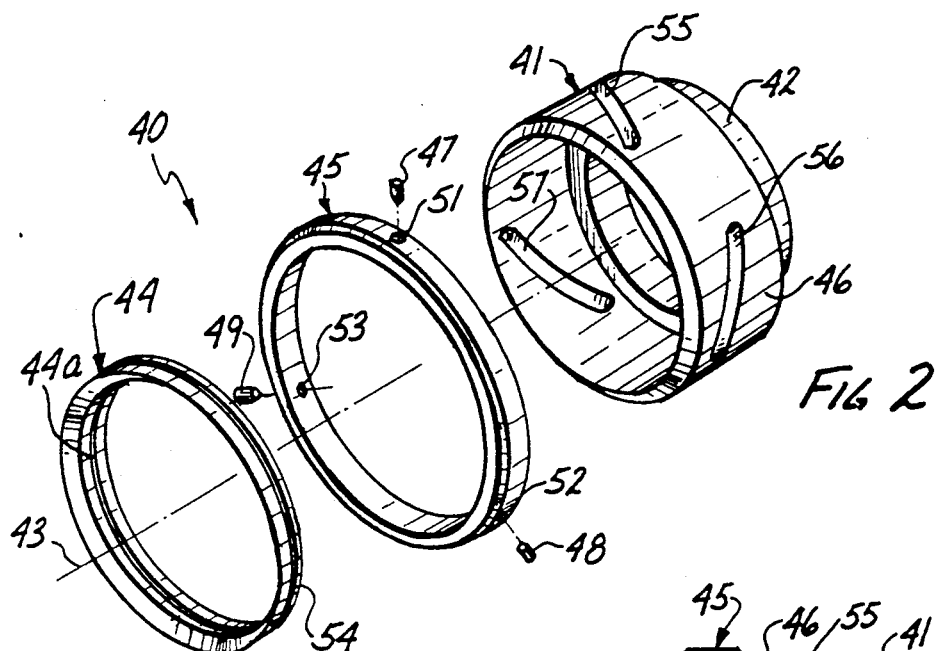
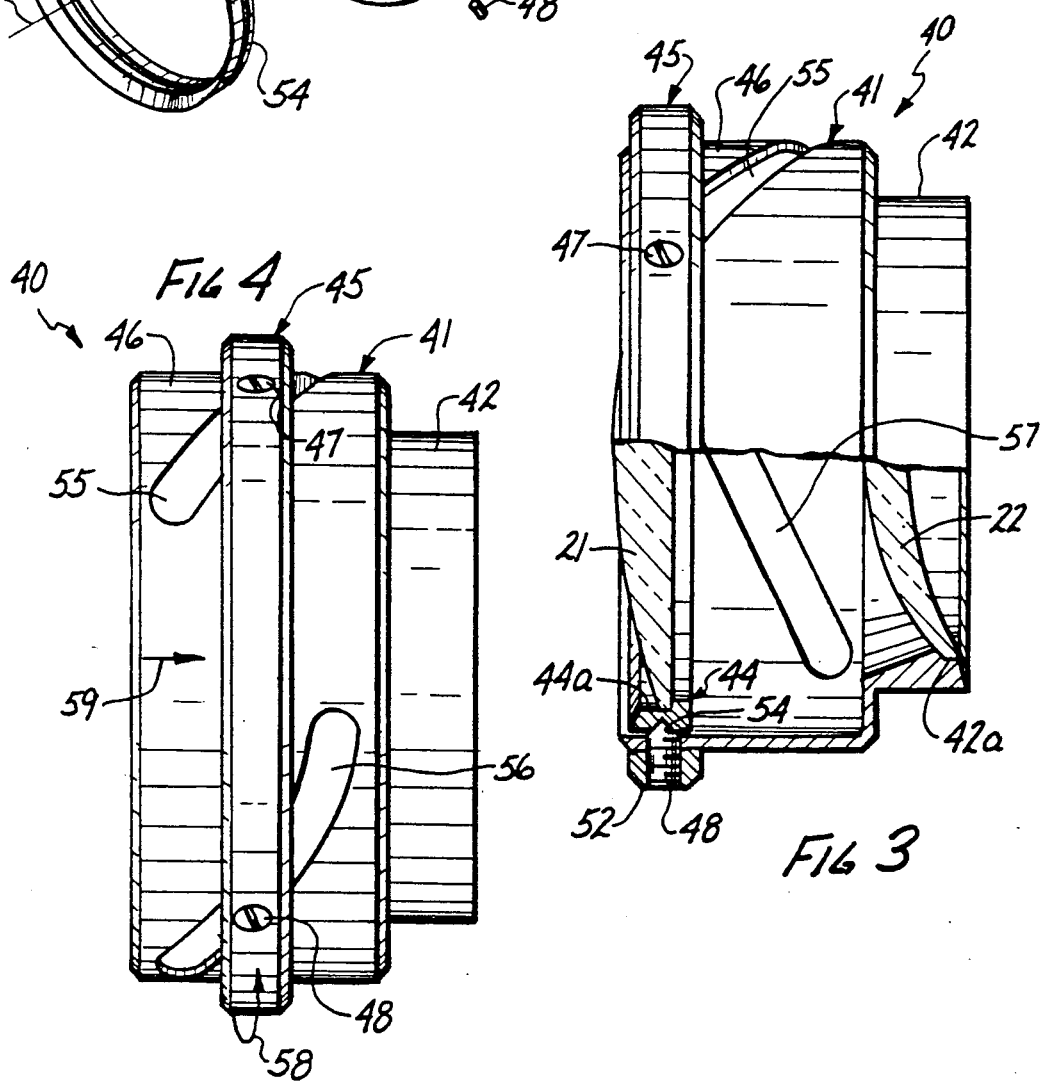
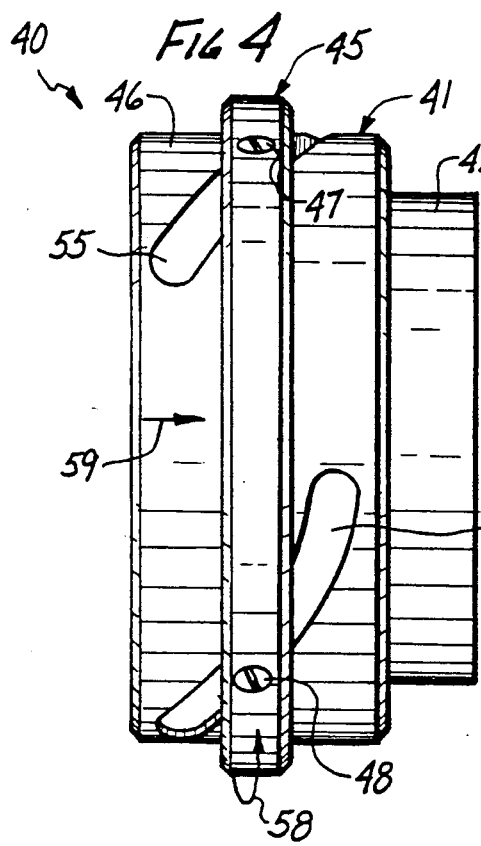

TELEDIOPTRIC LENS SYSTEM

This application is a division of application Ser. No. 141,482 filed Jan. 5, 1988, now U.S. Pat. No. 5,030,231.

BACKGROUND OF THE INVENTION

1. Technical Field

This invention relates generally to corrective lenses, and more particularly to an ocular telescopic lens system with a novel spectacle arrangement and improved intraocular lens for low-vision conditions such as macular degeneration.

2. Background Information

Macular degeneration affects the central retinal area known as the macula, and it can lead to a gradual or sudden loss of vision to the level of 20/200 or less. It may affect only about one-quarter to four square millimeters of the central retinal area, thereby leaving 95-99% of the retina unaffected. Thus, vision for reading and watching television can be lost while peripheral vision remains intact.

Telescopic systems that increase the retinal image size of a given object have been used in the past to compensate for this loss of vision. In addition, intraocular lenses having both converging and diverging portions have been used as part of the telescopic system, the diverging portion providing a telescopic effect over a restricted field of fixation when used with a converging spectacle lens, and the converging portion providing unrestricted peripheral vision when used without the spectacle lens. However, there are certain aspects of these lens arrangements that need improvement.

For example, the converging spectacle lens may have a power in the range of approximately +8 to +35 diopter or more, perhaps typically greater than +20 diopter, and a lens of this power may exhibit peripheral distortion that reduces the field of fixation, i.e. the amount the viewing axis of the eye can deviate from the optical axis of the spectacle lens. In addition, far and near vision adjustment by movement of the spectacle lens relative to the eye varies the vertex distance so that astigmatic correction, which is typically placed on the back surface of the lens, may be affected. Inasmuch as very steep surfaces have to be used, even small surface decentration can cause large amounts of aberration. Furthermore, a high power spectacle lens may be somewhat thick and heavy, and fabrication relatively expensive in view of such concerns as the more critical dimensions of the lens surface.

Consequently, it is desirable to have a new and improved spectacle lens arrangement for a teledioptric system that overcomes these concerns—one providing sufficient lens power and greater field of fixation that can be adjusted without varying the vertex distance and which utilizes a less heavy and less expensively fabricated lens.

Another aspect of existing telescopic systems that needs improvement, concerns the intraocular lens. An example of a lens having both converging and diverging portions is described in U.S. Pat. No. 4,666,446 to Koziol et al. The intraocular lens illustrated in that patent includes a forward lens surface having a converging or convex forward portion and a diverging or concave forward portion, as well as a rearward surface that includes converging and diverging rearward portions. The converging forward portion and the converging rearward portion combine to form a converging or positive lens, while the diverging forward portion and the diverging rearward portion combine to form a diverging or negative lens.

However, this arrangement could be improved to increase the field of view through the converging lens for off-axis images and to avoid discontinuities in the lens surface. Consequently, it is desirable to have an improved intraocular lens with these attributes.

SUMMARY OF THE INVENTION

This invention solves the problems outlined above with an intraocular lens and a spectacle arrangement that combine in a new and improved ocular telescopic lens system.

Briefly, the above and further objects of the present invention are realized by providing an ocular telescopic system that includes a bi-element spectacle lens arrangement. This results in less off-axis distortion with lenses that are less heavy and easier to fabricate, and power adjustment can proceed without varying the vertex distance. A novel intraocular lens is also provided that has a diverging portion on only one lens surface to thereby improve optical and physiological properties.

Generally, an ocular telescopic lens system constructed according to the invention includes an intraocular lens and a spectacle lens arrangement. According to a major aspect of the invention, the intraocular lens has a converging lens portion as well as a diverging lens portion that combines with multiple-element spectacles having anterior and posterior lenses arranged to converge light toward the diverging lens portion of the intraocular lens.

According to another aspect of the invention, there is provided multiple-element spectacles that include a lens system having at least an anterior lens and a posterior lens, and mounting components for mounting the anterior and posterior lenses on a spectacle frame so that light passes first through the anterior lens and then through the posterior lens in traveling to the eye. The anterior and posterior lenses may combine to serve as an objective lens and provide at least +8 diopter power.

According to yet another aspect of the invention, there is provided mounting components for adjusting a distance by which the anterior lens and the posterior lens are separated in order to cause a spectacle power change. These may enable adjustment of the anterior lens while the posterior lens remains generally fixed in position relative to a spectacle frame on which the lenses are mounted. Thus, adjusting the distance by which the anterior lens and posterior lens are separated does not vary the vertex distance by which the posterior lens is separated from the cornea of a user. In other words, a toric surface correcting for astigmatism is placed on the back surface of the posterior lens, and since the vertex distance remains constant, this correction remains unchanged.

Still another aspect of the invention provides an intraocular lens having an optic with a generally continuous rearward surface that combines with a first portion of the forward surface as the converging lens portion and with a second portion of the forward surface as the diverging lens portion. Of course, the intraocular lens can be with or without the multiple-element spectacles of this invention, as can the spectacles be used with or without the inventive intraocular lens.

A method of treating low vision according to the invention includes the steps of implanting in a patient an intraocular lens having a converging lens portion and a diverging lens portion, and then applying multiple-element spectacles to the patient so that light passes through the multiple-element spectacles to the diverging lens portion of the intraocular lens, with the multiple-element spectacles functioning as an objective lens.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 2 is a perspective view of one of the lens mounting components utilized on the multiple-element spectacles, shown disassembled;

FIG. 3 is an enlarged elevation view of the lens mounting, shown assembled with the anterior and posterior lenses;

FIG. 4 is an enlarged elevation view similar to FIG. 3 illustrating adjustment of the distance between lenses;

DESCRIPTION OF THE PREFERRED EMBODIMENT

Figure 1:
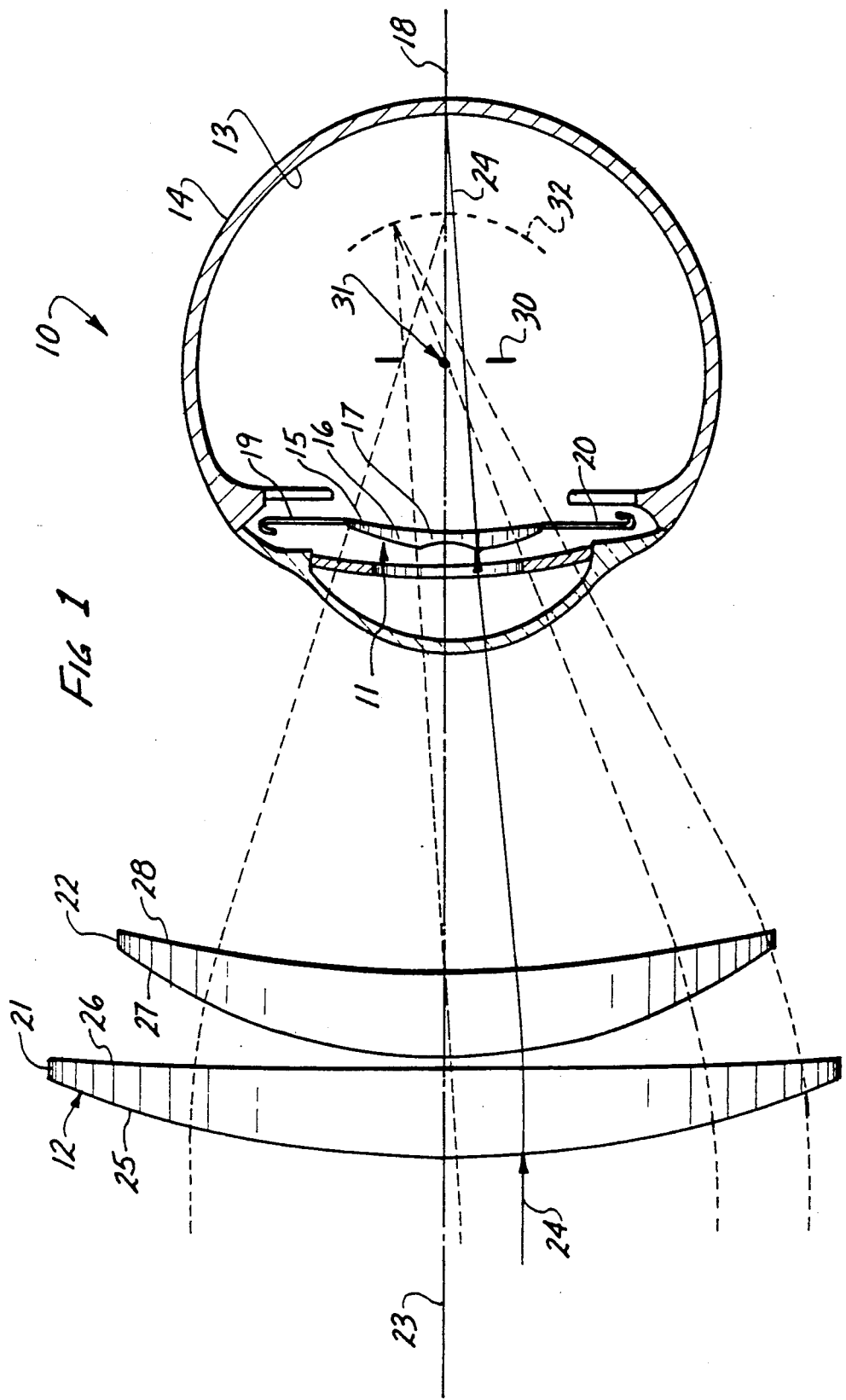
FIG. 1 of the drawings is a diagrammatic representation of an ocular telescopic lens system constructed according to the invention, including an eye with an intraocular lens that is superimposed on a spectacle ray diagram.

Referring now to FIG. 1, there is shown a diagrammatic representation of an ocular telescopic system 10 constructed according to the invention. Generally, the system 10 includes an intraocular lens 11 and a multiple element spectacle lens arrangement or spectacle lens system 12 that cooperate as a telescopic system to increase the image size on a retina 13 of an eye 14. These components function somewhat like the lenses described in U.S. Pat. No. 4,666,446 to Koziol et al., and that patent is incorporated herein by reference for the details provided.

The structure of the intraocular lens 11 is also similar in some respects to the intraocular lenses described in the Koziol et al. patent. It includes an optic 15 having a converging portion 16 and a diverging portion 17, and it is supported on the eye 14 in the optical path of the eye 14 by suitable means such as a pair of fixation members 19 and 20 so that it traverses the optical axis 18 of the eye 14 and is coaxial with the axis 18.

The converging portion 16 of the intraocular lens 11 normally has a power of from about +5 diopter to about +35 diopter, and it functions substantially in the same manner as the natural lens it replaces with respect to off axis images. The diverging portion 17 normally has a power of from about −40 diopter to about −70 diopter, and it cooperates with the spectacle lens system 12, which normally has a power of from about +20 diopter to about +35 diopter, to provide magnification in the range of about 2X to about 4X, depending on the power and vertex distance of the spectacle lens system 12. This is sufficient to enable many low-vision patients to read and watch television.

The spectacle lens system 12 includes an anterior lens 21 and a posterior lens 22. These are arranged coaxial with an optic or optical axis 23 of the spectacle lens system 12 and relative to each other so that with the optical axes 18 and 23 generally coinciding, the lenses 21 and 22 converge light toward the diverging portion 17 of the intraocular lens 15. As illustrated by a ray 24 in FIG. 1, light passes in sequence through the anterior lens 21, the posterior lens 22, and the intraocular lens 15 to the retina 13, with the anterior and posterior lenses 21 and 22 combining to serve as an objective lens of the telescopic system they form with the diverging portion 17 of the intraocular lens 15.

These surfaces are configured according to known lens design and fabrication techniques to achieve the converging optical characteristics described. However, with the multiple-element spectacle lens system 12, the anterior and posterior lenses 21 and 22 are lighter and easier to fabricate. In addition, they exhibit less aberration, especially peripheral distortion so that the field of fixation is increased over that achievable with a single high powered spectacle lens. Moreover, adjustment of the distance between the lenses can be made to vary the spectacle power without changing the vertex distance.

Preferably, the anterior lens 21 is a positive lens having a convex surface 25, and it is configured so that only the posterior lens 22 need be changed according to the patient's prescription. The posterior lens 22 has a convex forward surface 27 and a concave rearward surface 28, and the concave rearward surface 28 is configured according to the patient's prescription.

The anterior lens 21 may have a power of +8 diopter or more, or, depending upon the precise application of the multiple-element lens system 12 and the material used, the anterior and posterior lenses 21 and 22 may combine to have a power of at least +8 diopter, this being the power at which it becomes difficult to shape a lens to eliminate astigmatism resulting from an eye fixation off of the optical axis of the lens, i.e. the optical axis 18 of the eye and the optical axis 23 of the spectacles do not coincide.

The illustrated lenses 21 and 22 are designed for +23.5 diopter so that with an imaginary aperture stop 30 located at the center of rotation 31 of the eye 14 (approximately fourteen millimeters from the front surface of the cornea), light rays depicted in FIG. 1 by dashed lines produce an image at an imaginary image surface 32 approximately 1.7 millimeter beyond the center of eye rotation 31. The diverging portion 17 of the intraocular lens 11 is configured to have a power of approximately −53 diopter, and this combines with the +43 diopter of the cornea to result in −10 diopter, which positions the image on the retina 13.

In addition to reducing distortion in this way, distortion is reduced by mounting the anterior and posterior lenses 21 and 22 on a spectacle frame 34 (FIGS. 1a-1c) so that the posterior lens 22 is generally fixed relative to the eye 14 to hold the vertex distance generally constant.

The spectacle frame 34 is in many respects similar to a conventional pair of spectacle frames, but unlike conventional frames it includes a dummy lens 35 defining a mounting hole 36 and a dummy lens 37 defining a mounting hole 38. A pair of lens mounting arrangements or mountings 39 and 40 mount on the dummy lenses 35 and 37 within the holes 36 and 38 by suitable means, such as bonding, screws (not shown), or a snap-in fit. Each of the mountings 39 and 40 supports a lens 21 and a lens 22, and the mountings 39 and 40 are generally similar so that only the mounting 40 is described in further detail.

The mounting 40 mounts the lenses 21 and 22 on the spectacle frame 34 so that the position of the anterior lens 21 can be adjusted to provide a degree of accommodation (around one diopter, for example). Thus, it serves as means for mounting the anterior and posterior lenses 21 and 22 on a spectacle frame so that light passes first through the anterior lens 21 and then through the posterior lens 22 in traveling to the eye 14.

Generally, the mounting 40 includes a first member or outer case 41 (FIGS. 2-5) that is dimensioned and arranged to be mounted on the spectacle frame 34 for this purpose, and it combines with components subsequently described that mount the anterior lens 21. The outer case 41 serves as posterior lens support means for supporting the posterior lens 22 in generally fixed relationship to the spectacle frame 34. For this purpose, the illustrated outer case 41 includes a cylindrically-shaped rearward portion 42 that is dimensioned and arranged to receive the posterior lens 22 in the position illustrated in FIG. 3. The posterior lens 22 may be retained in this position by suitable means, such as a snap-in fit within an inwardly facing annular groove 42A in the forward portion 42 (FIG. 3).

Figure 1A:
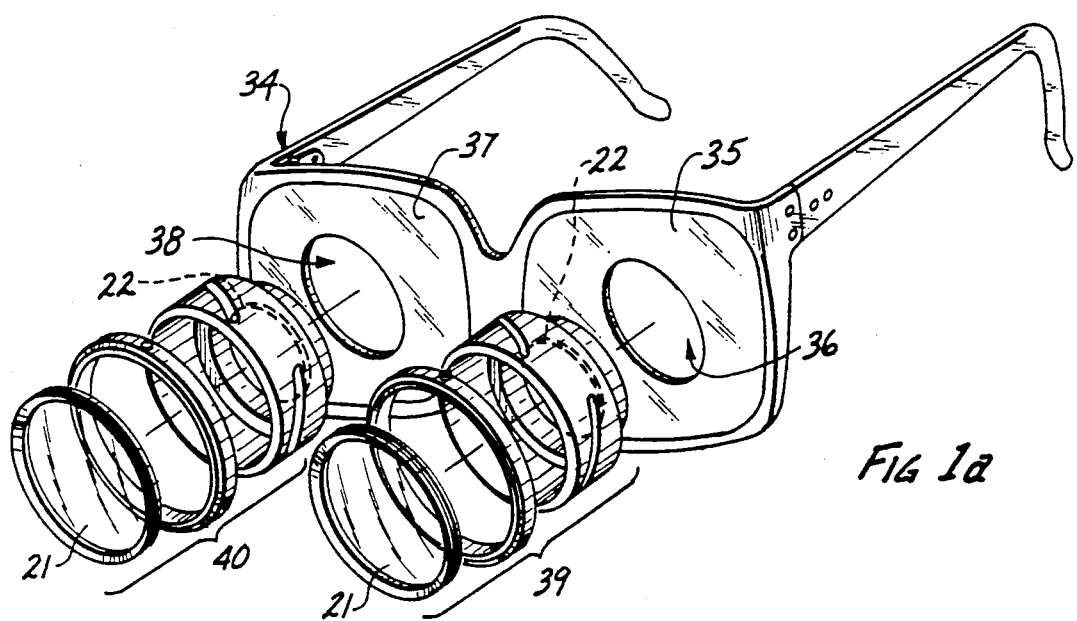
FIGS. 1a-1c show various aspects of a pair of multiple-element spectacles utilized in the ocular telescopic lens system.
Figure 1B:
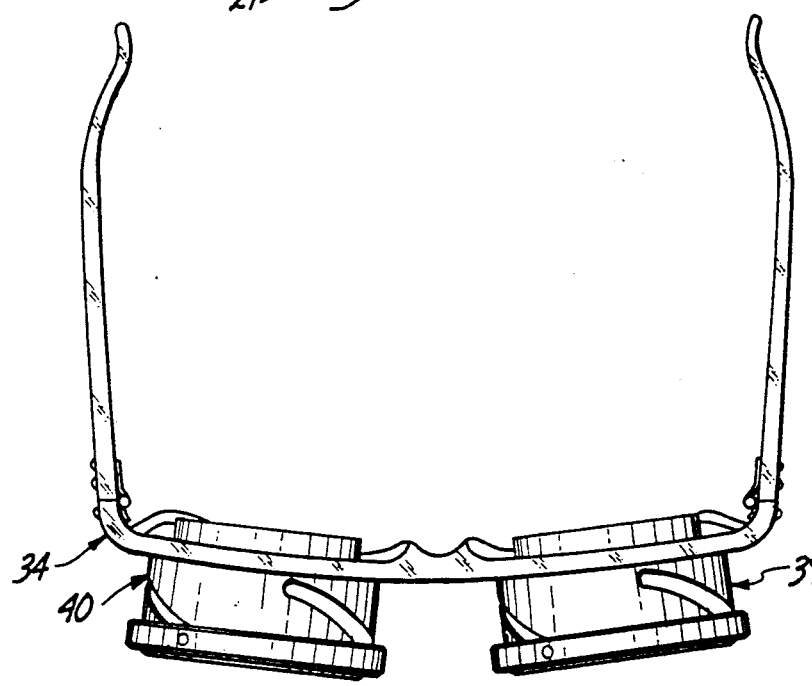
Figure 1C:
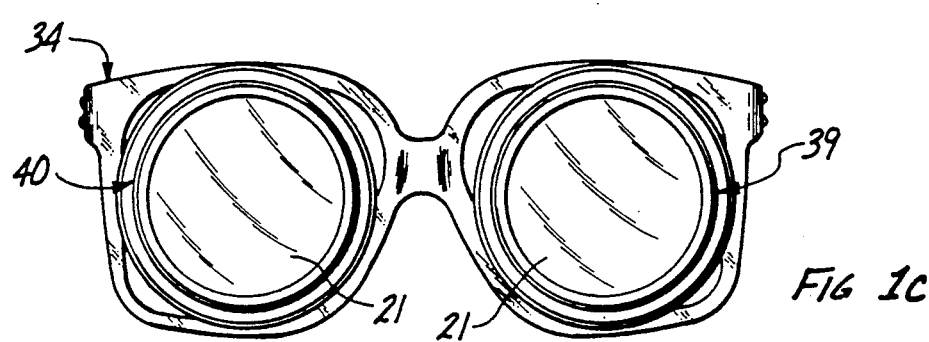

In addition, the rearward portion 42 is dimensioned and arranged to be mounted on the dummy lens 37, which is a dummy lens in the sense that its optical properties are unimportant for it to serve as a mechanical adapter that mounts the outer case 41 on the spectacle frame 34. The rearward portion 42 fits within the hole 38 in the dummy lens 37, and the dummy lens 37 fits into the spectacle frame 34 as shown in FIGS. 1a-1c, with a snap-in fit, for example.

As an idea of size, the rearward portion 42 of the outer case 41 may have an outside diameter of approximately three and one-half centimeters, and extend along an axis 43 (FIG. 2) about two and one-half centimeters. This results in a sufficiently small and light mounting 40 for attachment to a conventional spectacle frame. Of course, other sizes and other mounting arrangements for mounting the outer case 41 on a spectacle frame can be employed without departing from the inventive concepts disclosed.

The mounting 40 includes a second member or inner sleeve 44. The inner sleeve 44 is dimensioned and arranged to be mounted on the outer case 41, and it serves as means for supporting the anterior lens 21. For this purpose, the illustrated sleeve 42 takes the form of a ring that is dimensioned and arranged to receive the anterior lens 21 in the position illustrated in FIG. 3, and to fit generally concentrically within the outer case 41. The anterior lens 21 may also be retained in position by suitable means such as a snap-in fit within an inwardly facing annular groove 44A (FIGS. 2 and 3).

The mounting 40 also includes mounting means for moveably mounting the inner sleeve 44 on the outer case 41 so that it is aligned with the posterior lens 22 in the sense that the optical axis of the anterior lens 21 is generally aligned with the optical axis of the posterior lenses 22 as the optical axes of the spectacle lens system 12 mentioned above with respect to FIG. 1.

In other words, all axes generally align with the axis 43 in FIG. 1, and the mounting means also functions to moveably mount the inner sleeve 44 so that the anterior lens 21 can be moved axially relative to the posterior lens 22, along the axis 43. This enables the user to adjust the distance between the anterior and posterior lenses 21 and 22, and this is accomplished in the illustrated mounting 40 with a third member or slide ring 45.

The slide ring 45 is dimensioned and arranged to fit generally concentrically over a forward portion 46 of the outer case 41. A plurality of retainer members or screws 47-49 pass through a corresponding plurality of threaded holes 51-53 in the slide ring 45 to engage an annular groove 54 in the inner sleeve 44 (FIGS. 1 and 3). This retains the inner sleeve 44 on the outer case 41.

The screws 47-49 pass through a corresponding plurality of elongated openings or grooves 55-57 in the outer case 41 that extend both circumferentially and axially as illustrated. When the slide ring 45 is rotated in the direction of an arrow 58 in FIG. 4, the slide ring 45 and inner sleeve 44 advance axially in the direction of an arrow 59. Reversing the direction of rotation reverses the direction of movement.

This arrangement serves as means for enabling rotation of the inner sleeve 44, and for causing the anterior lens 21 to move axially when the inner sleeve 44 is rotated. This, in turn, enables adjustment of a distance by which the anterior lens 21 and the posterior lens 22 are separated, and this is done while the posterior lens 22 remains generally fixed in position relative to a spectacle frame on which the anterior and posterior lenses 21 and 22 are mounted so that adjusting this distance does not vary a vertex distance by which the posterior lens 22 is separated from a cornea.

Figure 7:
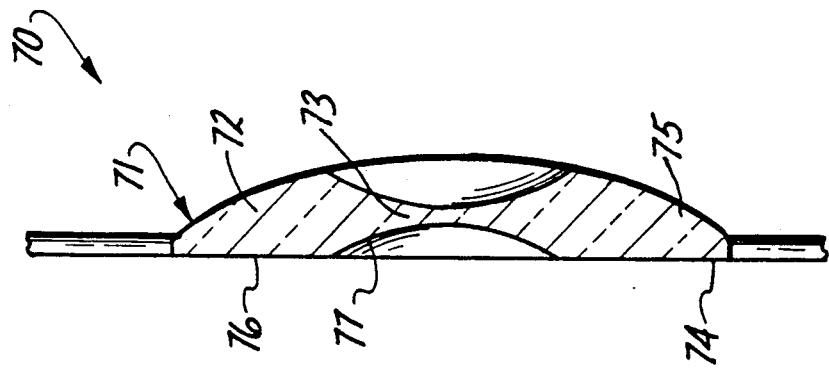
FIG. 7 is a similar enlarged cross section view of an intraocular lens constructed according to the prior art.
Figure 6:
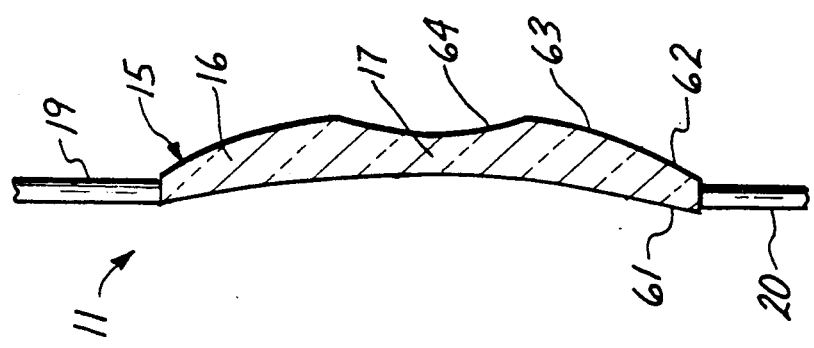
FIG. 6 is an enlarged cross section view of the optic portion of the intraocular lens taken on line 6—6 of FIG. 5.
Figure 5:
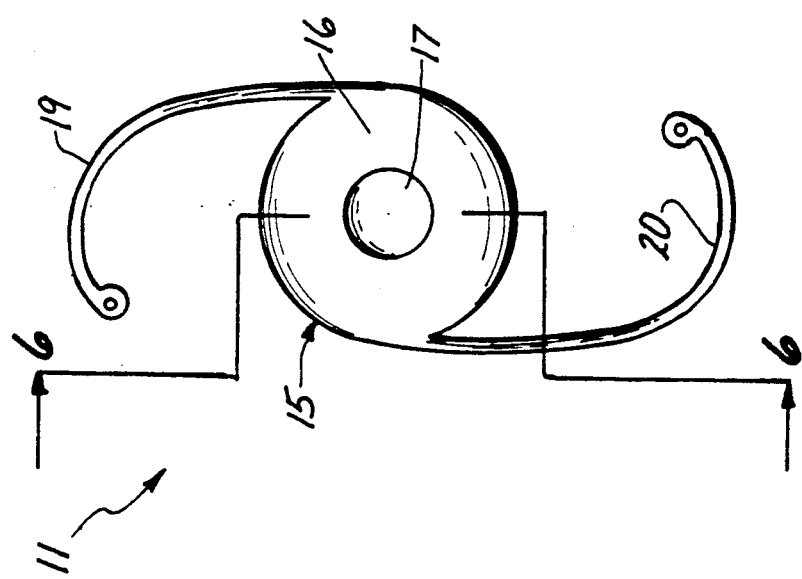
FIG. 5 is a plan view of an intraocular lens utilized in the ocular telescopic lens system.

Considering now the intraocular lens 11 in further detail (FIGS. 5-7), it is in some respects similar to the intraocular lenses described in the Koziol patent referenced above, and that patent is also incorporated herein for the details of intraocular lens construction provided.

Generally, the intraocular lens 11 includes the optic 15, which is fabricated from a biocompatible material according to known techniques so that it is dimensioned and arranged to be retained in an eye in the optical path of the eye, i.e. traversing the optical axis 18 of the eye 14 in FIG. 1. One or more fixation members, such as the fixation members 19 and 20 are suitably attached to the optic 15 in a known manner to serve as fixation means for supporting the optic 15 in the eye 14.

The converging portion 16 and the diverging portion 17 of the optic 15 that were mentioned previously with reference to FIG. 1 extend between rearward and forward surfaces 61 and 62 of the optic 15. The rearward surface 61 is generally continuous and concave while the forward surface 62 includes a first or generally convex portion 63 and a second or generally concave portion 64. The converging portion 16 extends between the convex portion 63 and the rearward surface 61, while the diverging portion 17 extends between the concave portion 64 and the rearward surface 61. The optic 15 and the diverging portion 17 are generally circular. The converging portion 16 is annular, i.e., it is coaxial with and surrounds the diverging portion 17.

This results in an optic 15 having better optical and physiological properties because there are fewer discontinuities in the rearward surface 61. It also results in better off-axis vision as illustrated in conjunction with a prior art intraocular lens 70 in FIG. 7.

The lens 70 includes an optic 71 having a converging portion 72 and a diverging portion 73 that extend between a rearward surface 74 and a forward surface 75. However, the rearward surface 74 is not generally continuous. Instead, it includes both a generally planar first portion 76 that is part of the converging portion 72 of the optic 71, and a generally concave second portion 77 that is part of the diverging portion 73 of the optic 71. This arrangement introduces discontinuities in the rearward surface 74 that can affect optical properties of the lens 11.

In addition, this arrangement may reduce off-axis vision because it reduces the size of the converging portion 72. In other words, the second portion 77 occupies a portion of the rearward surface 74 that is in the path of light rays that could otherwise be converged toward the retina 13 of the eye 14 in FIG. 1.

The intraocular lens 11 of this invention results in better off-axis vision because the rearward surface 61 is generally continuous, with a concave configuration that functions as the rearward surface of both the converging portion 16 and the diverging portion 17.

In order to treat a low vision condition such as macular degeneration according to the invention, the intraocular lens 11 is implanted and a multiple-element spectacles applied to result in the ocular telescopic system 10. In line with this, the method of the invention includes the steps of implanting in a patient an intraocular lens having a converging lens portion and a diverging lens portion, and then applying multiple-element spectacles to the patient so that light passes through the multiple-element spectacles to the diverging lens portion of the intraocular lens, with the multiple-element spectacles functioning as an objective lens.

Thus, this invention solves many problems associated with the prior art. It provides an intraocular lens and a spectacle arrangement that combine in a new and improved ocular telescopic lens system for low-vision conditions such as macular degeneration. These components result in less peripheral distortion. The lenses are less heavy and easier to fabricate. Adjustment can proceed without varying the vertex distance, and the novel intraocular lens provides improved optical and physiological properties.

Although an exemplary embodiment of the invention has been shown and described, many changes, modifications, and substitutions may be made by one having ordinary skill in the art without necessarily departing from the spirit and scope of this invention.

What is claimed is:

1. Spectacles comprising:
 a spectacle frame;
 a tubular outer case coupled to the spectacle frame;
 a posterior lens carried by said outer case in axially fixed relationship to the outer case;
 an inner sleeve within the outer case anteriorly of the posterior lens;
 an anterior lens carried by the inner sleeve in axial alignment with the posterior lens;
 a ring receiving the outer case; and
 said outer case having an opening adjacent the ring which extends both circumferentially and axially, said ring being coupled to the inner sleeve through the opening and being rotatable relative to the outer case whereby rotation of the ring relative to the outer case moves the inner sleeve and the anterior lens axially.

2. Spectacles as defined in claim 1 including a dummy lens carried by the spectacle frame and having a mounting hole, said outer case being received in said mounting hole.

3. Spectacles as defined in claim 2 wherein the outer case has a rearward portion and a forward portion which has larger radial dimensions than the rearward portion, said rearward portion is received in the hole of the dummy lens and the ring receives the forward portion.

4. Spectacles as defined in claim 1 wherein the outer case has a plurality of said openings and a plurality of fasteners extend through the openings respectively to couple the ring to the liner sleeve.

5. Spectacles comprising:
 a spectacle frame;
 first and second tubular outer cases coupled to the spectacle frame;
 first and second posterior lenses carried by said first and second outer cases respectively in axially fixed relationship to the associated outer case;
 first and second inner sleeves within the first and second outer cases respectively, each of said inner sleeves being located anteriorly of the associated posterior lens;
 first and second anterior lenses carried by the first and second inner sleeves respectively in axial alignment with the associated posterior lens;
 first and second rings receiving the first and second outer cases respectively; and
 each of said outer cases having an opening adjacent the associated ring which extends both circumferentially and axially, the first and second rings being coupled to the first and second inner sleeves through the opening in the associated outer case and being rotatable relative to the associated outer case whereby rotation of each ring relative to the associated outer case moves the associated inner sleeve and anterior lens axially.

* * * * *

UNITED STATES PATENT AND TRADEMARK OFFICE
CERTIFICATE OF CORRECTION

PATENT NO. : 5,088,809
DATED : February 18, 1992
INVENTOR(S) : Valdemar Portney

It is certified that error appears in the above—identified patent and that said Letters Patent is hereby corrected as shown below:

Column 8, line 28, delete "liner" and replace with -- inner -- .

Signed and Sealed this

Thirty-first Day of August, 1993

Attest:

BRUCE LEHMAN

*Attesting Officer*

*Commissioner of Patents and Trademarks*